United States Patent [19]

Kessler et al.

[11] Patent Number: 5,684,252
[45] Date of Patent: Nov. 4, 1997

[54] METHOD AND APPARATUS FOR ULTRASONIC INSPECTION OF ELECTRONIC COMPONENTS

[75] Inventors: Lawrence W. Kessler, Buffalo Grove; Daniel W. Micek, Norridge; John Billone, Des Plaines, all of Ill.

[73] Assignee: Sonoscan, Inc., Bensenville, Ill.

[21] Appl. No.: 678,607

[22] Filed: Jul. 15, 1996

[51] Int. Cl.⁶ .................................................. G01N 29/04
[52] U.S. Cl. .................................................. 73/618; 73/620
[58] Field of Search ........................... 73/620, 629, 621, 73/627, 633, 644, 582, 592, 596, 598, 600, 618, 41.2, 41.3, 41.4, 45.5; 324/514

[56] References Cited

U.S. PATENT DOCUMENTS

| | | | |
|---|---|---|---|
| 3,850,027 | 11/1974 | Nakanishi | 73/600 |
| 3,886,793 | 6/1975 | Cramer | 73/601 |
| 3,898,839 | 8/1975 | White | 73/644 |
| 4,008,602 | 2/1977 | Love | 73/620 |
| 4,208,915 | 6/1980 | Edwards | 73/620 |
| 4,332,016 | 5/1982 | Berntsen | 73/628 |
| 5,431,054 | 7/1995 | Reeves | 73/641 |

*Primary Examiner*—Christine K. Oda
*Attorney, Agent, or Firm*—Dorn, McEachran, Jambor & Keating

[57] ABSTRACT

A method and apparatus for non-destructive ultrasonic inspection in which a plurality of integrated circuits or other electronic components laid out in a fixed pattern on a liquid-permeable tray are moved along an inspection path through a scanning station. In the scanning station the electronic components are repetitively scanned by an ultrasonic beam from a transmitter/receiver moving rapidly back and forth across the inspection path; an ultrasonic coupling liquid (usually water) continuously flows along the beam path; the coupling liquid also flows along the surfaces of the electronic components opposite the beam path. The tray of electronic components is air dried as it emerges from the scanning station. Both reflected and "through" ultrasonic signals can be collected to disclose any anomalies present in the electronic components. A screen may be used to assure retention of the electronic components in the desired pattern on a tray.

14 Claims, 3 Drawing Sheets

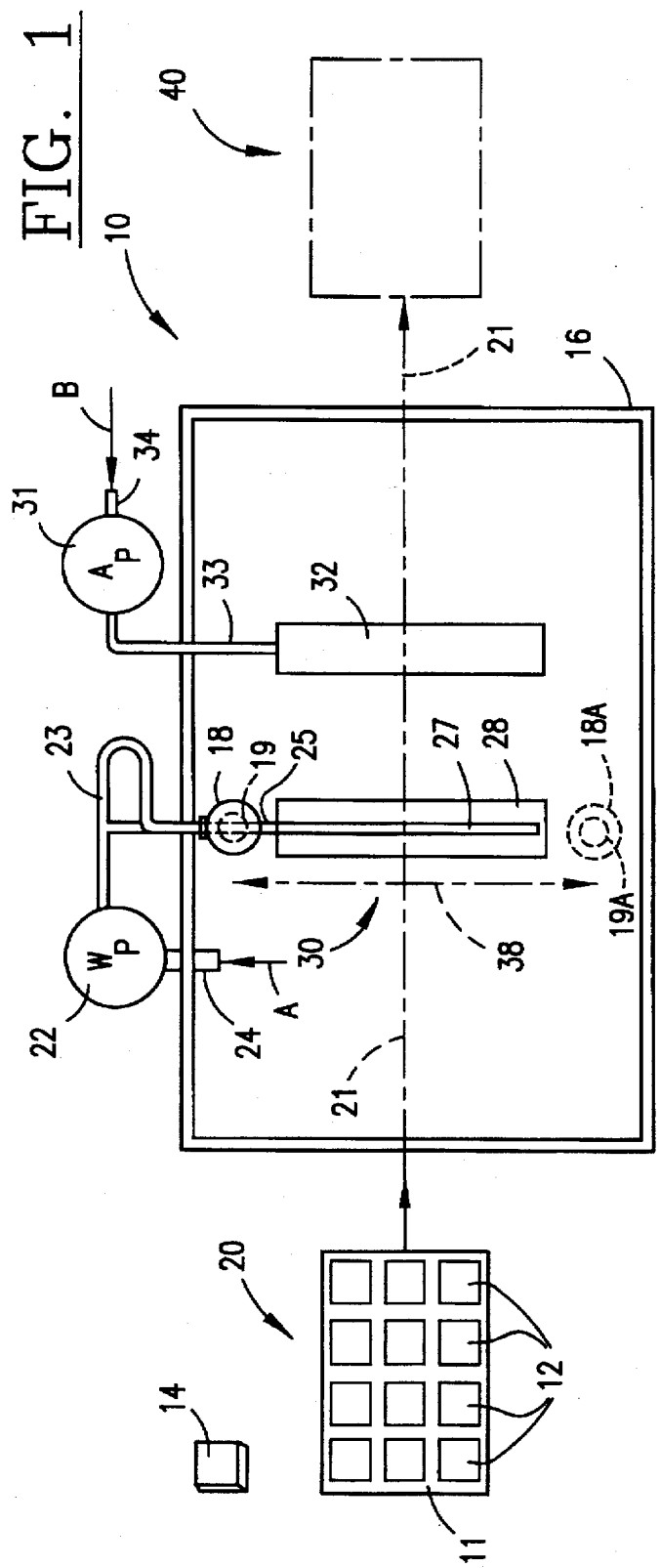
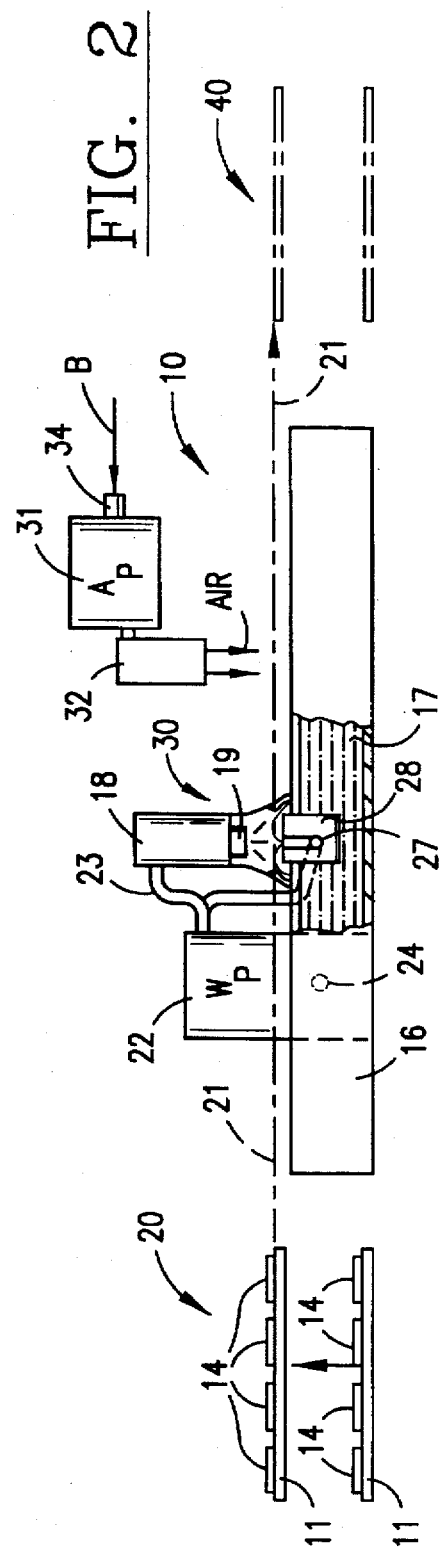

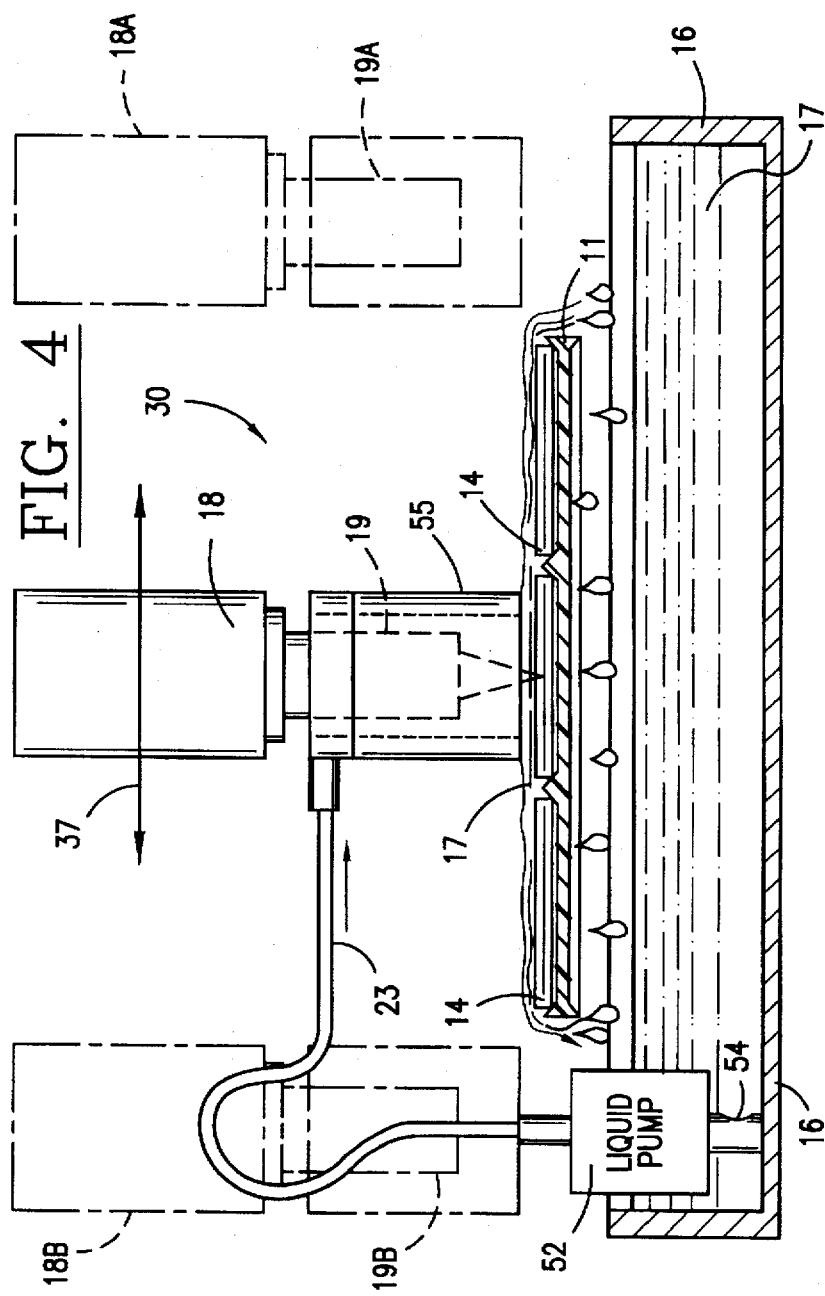

METHOD AND APPARATUS FOR ULTRASONIC INSPECTION OF ELECTRONIC COMPONENTS

BACKGROUND OF THE INVENTION

Ultrasonic inspection of integrated circuits, capacitors, and other electronic components has been utilized for several years. In part, the broad use of this technique is based on the fact that ultrasonic inspection is non-destructive. Delaminations within the electronic components, especially integrated circuits, or other anomalies affecting internal electrical leads, are the usual subjects of this form of inspection. One hundred percent inspection is desirable because incomplete electrical connections within a component cannot be seen and may render the component unusable.

Coupling an ultrasonic beam or "field" to an electronic component usually requires a liquid medium for inspection of electrical connections within that component; in air or other gaseous media, losses for the ultrasonic signal are often too great. In many known ultrasonic inspection systems the component requiring inspection is immersed in a tank of water or some other liquid coupling medium. See, for example, the systems disclosed in Kessler et al. U.S. Pat. No. 4,518,992 and Cichanski U.S. Pat. Nos. 4,781,067 and No. 4,866,986. For large components, tested one at a time, this is not an appreciable handicap. For simultaneous inspection of plural small, light weight electronic components, however, immersion of a tray or other carrier bearing the components may present substantial difficulties. See, for example, the pending Kessler et al. U.S. patent application Ser. No. 08/515,601, filed Aug. 16, 1995. One hundred percent inspection is often needed, due to frequent anomalies (e.g., delaminations) in the electronic components. Repeated inspections may be required for some electronic components having internal connections at different levels within each component.

A further problem is presented in that inspection using only reflected ultrasonic signals may be inconclusive; that is, the reflection returns, by themselves, may be inconclusive with respect to some delaminations. Using returns from reflected ultrasonic signals in conjunction with ultrasonic signals that are transmitted through the electronic components can afford more reliable and consistent inspection results.

SUMMARY OF THE INVENTION

It is an object of the invention, therefore, to provide a new and improved method and apparatus for ultrasonic non-destructive inspection of a plurality of small integrated circuits, or other electronic components, that does not require immersion of the inspected components in a tank of water or other coupling liquid medium.

Another object of the invention is to provide for adjustment of the position of the transmitter/receiver in an ultrasonic inspection system to allow for inspection of electronic components of differing dimensions or for inspection of plural levels within a group of electronic components.

A further object of the invention is to provide an ultrasonic inspection system for inspecting electronic components, using either or both reflected ultrasonic signals and ultrasonic signals modified by passing through the components, that is reliable, effective, and relatively inexpensive and that has a high throughput rate.

Accordingly, in one aspect the invention relates to a method of non-destructive ultrasonic inspection of a plurality of encapsulated electronic components arranged in a predetermined pattern on a tray, the method comprising the steps of:

A. advancing a tray bearing a plurality of electronic components in a predetermined pattern along a predetermined inspection path from a first station through a scanning station;

B. maintaining a flow of a coupling liquid medium from an ultrasonic transmitter toward the tray in the scanning station, along a beam path approximately normal to the inspection path;

C. energizing the ultrasonic transmitter to transmit an ultrasonic irradiation beam from the transmitter along the beam path to insonify electronic components on the tray in the scanning station;

D. moving the transmitter rapidly back and forth along a scanning path that is transverse to both the inspection path and the beam path;

E. collecting ultrasonic signals from components on the tray at one end of the beam path;

F. processing the collected signals from step E to identify and locate delaminations in the electronic components; and G. blowing a drying gas, usually air, onto the tray to remove the coupling fluid medium from the tray and from the electronic components on the tray;

In another aspect, the invention relates to a non-destructive ultrasonic inspection apparatus for inspecting a plurality of encapsulated electronic components positioned in a predetermined pattern upon a tray. The inspection apparatus comprises means for advancing a component-bearing tray, at a predetermined speed, along a horizontal inspection path from a first station through a scanning station containing an ultrasonic transmitter having a beam emission orifice facing toward the inspection path, but spaced therefrom. The tray-advancing means including two conveyor belts located at opposite sides of the inspection path. The inspection apparatus further comprises means for energizing the transmitter so that the transmitter transmits an ultrasonic irradiation beam along a vertical path impinge upon and insonify each electronic component on the tray at the scanning station; fluid flow means are employed to maintain a flow of an ultrasonic coupling fluid along the beam path from the beam emission orifice of the ultrasonic transmitter onto one side of the tray in the scanning station. The inspection apparatus also includes drive means for moving the transmitter rapidly back and forth along a scanning path transverse to the inspection path. An ultrasonic receiver is located in the scanning station in position to intercept ultrasonic signals modified by the electronic components; the output of the receiver is used to identify and locate delaminations and other anomalies in the electronic components.

BRIEF DESCRIPTION OF THE DRAWING

FIG. 1 is a simplified schematic plan view of an ultrasonic inspection system according to the invention;

FIG. 2 is a simplified schematic elevation view of the system of FIG. 1;

FIG. 4 is a simplified cross-section elevation taken approximately along line 4—4 in FIG. 1, eliminating the through-beam detector;

FIGS. 4A and 4B are diagrams of alternative scanning patterns usable in the invention.

DESCRIPTION OF THE PREFERRED EMBODIMENTS

Figure 5:
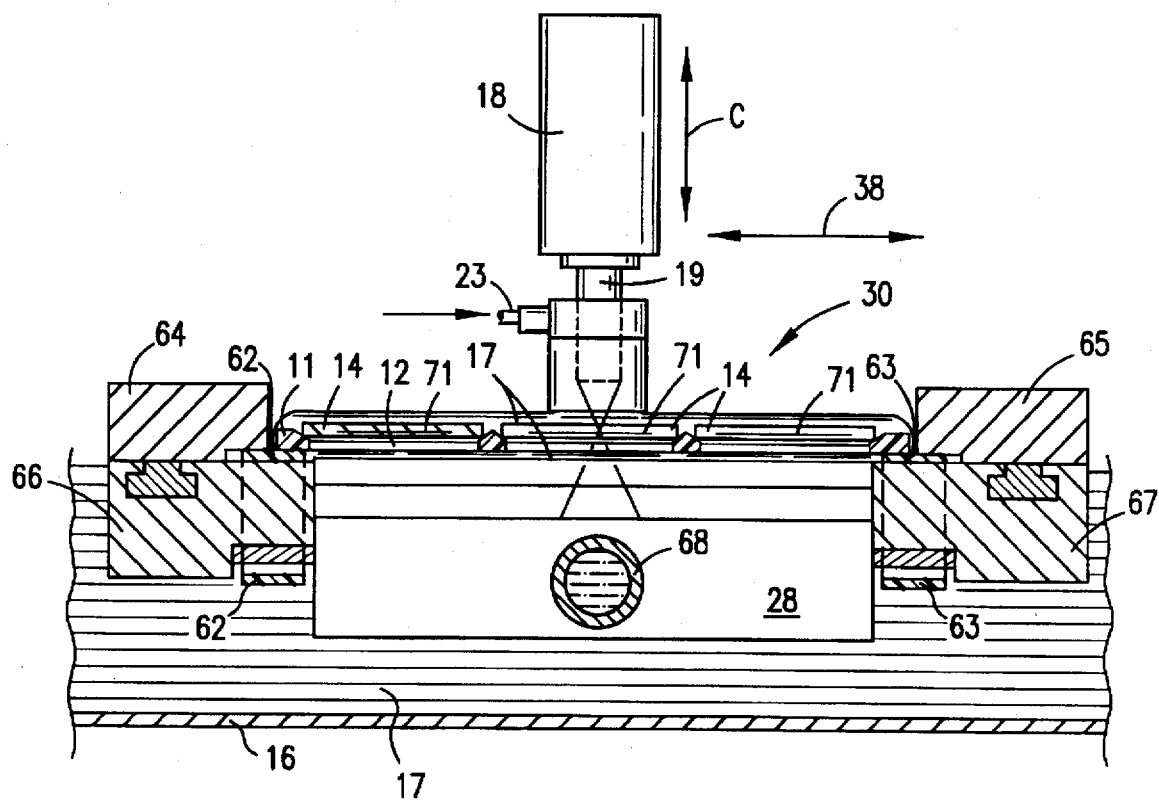
FIG. 5 is a cross-section similar to FIG. 4 but on a larger scale and with greater detail.

FIGS. 1 and 2 illustrate a system 10 for carrying out ultrasonic inspection of plural encapsulated electronic components in accordance with the method of the invention. System 10 of FIG. 1 and 2 also comprises a simplified illustration of the inspection apparatus of the invention.

System 10 starts with one or more flat, liquid-permeable trays 11, familiarly known as JEDEC trays. Each tray 11 includes a plurality of openings or receptacles 12; because the receptacles 12 are open, they can and do pass liquid freely through the tray. Thus, each tray 11 is liquid-permeable. Each tray 11 has its receptacles 12 filled with a plurality of encapsulated electronic components 14, usually integrated circuits having plural internal electrical connections. The purpose of system 10 is to inspect each of the electronic components 14 to determine whether they have any internal anomalies, usually delaminations affording incomplete or unreliable electrical connections. The electronic components 14 are usually flat and rectangular, as shown, but other component configurations may be inspected, using appropriate trays.

System 10 further includes a large tray or tank 16 that is filled with a liquid coupling medium 17 as shown in FIG. 2. The liquid coupling medium has been omitted in FIG. 1 to permit better illustration of other components of system 10. Usually, the liquid coupling medium is water or an aqueous solution; any non-corrosive liquid medium affording acceptable ultrasonic coupling characteristics may be employed in system 10.

System 10 of FIGS. 1 and 2 further comprises an ultrasonic transmitter/receiver transducer 18 having a beam emission orifice 19 facing toward the inspection path 21 through the system. The transmitter/receiver 18 has an external housing connected to a pump 22 by a lengthy, flexible liquid tube or conduit 23; the full length of tube 23 is not shown. Pump 22 has an inlet 24 connected through a side wall of tank 16 to draw water or other liquid coupling medium from the supply 17 in tank 16 as indicated by arrow A in FIG. 1. Alternative positions for transducer 18 and its emission orifice 19 are indicated, in FIG. 1, by dash outlines 18A and 19A.

Pump 22 has a further outlet connection 26 to a central channel 27 in an elongated ultrasonic receiver 28 located in tank 16 below the inspection path 21. Through conduit 23 the liquid coupling medium is dispensed downwardly from transmitter/receiver 18 over the top of a tray traversing path 21, as described more fully hereinafter. The liquid coupling medium is also impelled upwardly from the central conduit 27 in an elongated receiver 28 against the bottom of the tray. In both instances, the impetus for the liquid is supplied by pump 22. Two pumps could be used; one is usually adequate.

System 10 also includes another pump, however, the air pump 31 (FIG. 1) that supplies drying air to an elongated manifold or "air knife" 32 extending transversely of path 21 over tank 16. Manifold 32 is long enough to span the entire width of a tray 11. The drying air is supplied from pump 31 to manifold 32 through a conduit 33, FIG. 1. Of course, pump 31 has an appropriate inlet 34, which supplies ambient air to the pump as indicated by arrow B. A drying gas other than air may be employed, but is economically undesirable.

Figure 3:
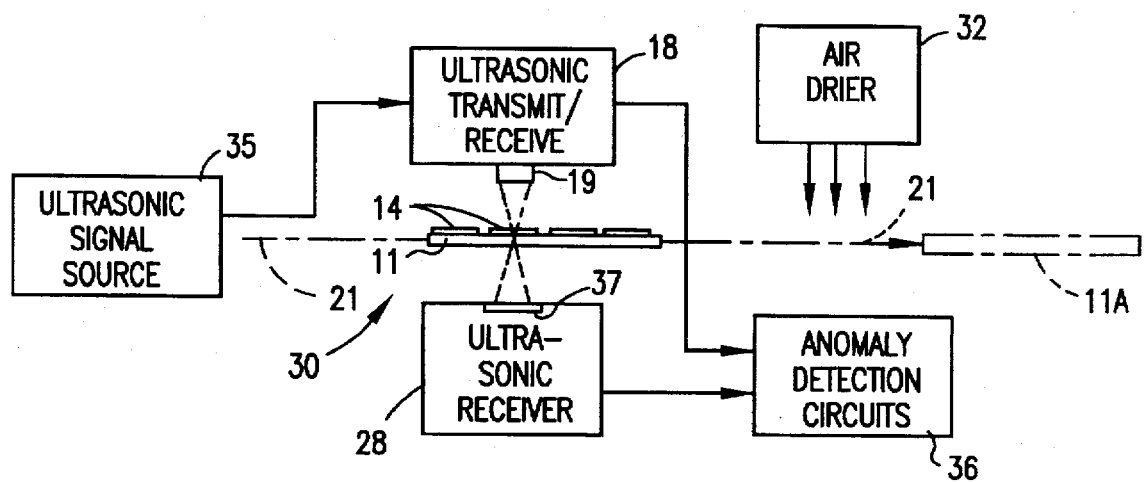
FIG. 3 is a simplified block diagram of the ultrasonic circuits for the system of FIGS. 1 and 2.

Operation of the inspection system 10 of FIGS. 1 and 2 can now be considered, with further reference to the block diagram presented in FIG. 3. At the outset, the ultrasonic transmitter/receiver transducer 18 is actuated by an appropriate signal from a signal source 35, FIG. 3. Signal source 35 and transmitter/receiver 18 may be combined in one unit. When energized, transducer 18 generates an ultrasonic beam which is directed downwardly, through emission orifice 19 along a vertical beam path that is transverse to inspection path 21, toward the lens 37 of ultrasonic receiver 28. The ultrasonic beam is usually pulsating, with intervals between transmitted pulses used to receive reflections from the electronic components 14. At this juncture any output signals developed by the two receivers 18 and 28 are meaningless and may be ignored in the anomaly detection circuits 36 (FIG. 3), which are connected to the outputs of both of the ultrasonic receivers.

The next step is to advance tray 11 from a first station 20, FIGS. 1 and 2, along the generally horizontal inspection path 21 toward a scanning station 30 near the center of tank 16. Tray 11 carries a plurality of the electronic components 14 to be inspected, usually with one component 14 in each receptacle 12 in the tray. Thus, components 14 are arranged in a predetermined pattern on the tray. Ordinarily, the receptacles 12 in tray 11 are all filled; however, if one or more of the receptacles in the tray are open, it is a simple matter to take appropriate action to set the anomaly detection circuits 36 (FIG. 3) to ignore inputs from the empty tray receptacles.

As a tray 11 enters scanning station 30 it is irradiated with the pulsed ultrasonic beam from orifice 19 of transmitter/receiver 18. A part of the ultrasonic beam is reflected back to and received through orifice 19 of transmitter/receiver 18; another part of the ultrasonic beam is transmitted through the components 14 on tray 11 and impinges upon the elongated second receiver 28. The ultrasonic beam may be focussed at a predetermined vertical level, within components 14, where a delamination or other anomaly is most likely to occur.

The speed of tray 11 along path 21 may be constant so that detection circuits 35 can accurately locate any detected anomaly. Typically, the rate of tray movement along path 21 may be about 6 inches (15.24 cm) per minute. The ultrasonic beam from transducer 18 is coupled to the electronic components 14 on tray 11 by the continuous flow of the liquid coupling medium 17 flowing down along the vertical beam path from orifice 19 to the lens 36 of receiver 28; see FIGS. 2 and 3. Moreover, the bottom of tray 11, when the tray is passing through scanning station 30, intercepts the upward flow of the liquid coupling medium 17 from receiver 28. That is, the ultrasonic beam is effectively coupled to the top surface of each component 14 on tray 11; the bottom surface of each component 14 is also effectively coupled to the receiver 28 by the fluid flowing upwardly out of conduit 27 in receiver 28.

While tray 11 is traversing scanning station 30, transmitter/receiver 18 is moved rapidly back and forth in a generally horizontal direction across inspection path 21, along a scanning path 38, at a substantially constant speed. The scanning speed may be of the order of fifty to one hundred inches (127–254 cm) per second. As a consequence, each component 14 on tray is scanned repeatedly as the tray moves through the scanning station 30. Usually, the scanning speed for movement of transducer 18 back and forth along path 37 is appreciably higher than the rate at which tray 11 moves through the scanning station along path 21. Typically, the scanning time for a tray may be about 2.5 minutes.

In the preferred system 10, two ultrasonic signals are continuously collected during operation of system 10.

Reflected ultrasonic signals from components 14 are collected, by receiver circuits in transducer 18, at the upper end of the path of the ultrasonic beam, the end adjacent the point of transmission for the ultrasonic beam. Other ultrasonic signals that pass through the components 14 on tray 11 are collected by the second receiver 28. Both of these signals, reflected and "through" signals, are supplied to the anomaly detection circuits 36 (FIG. 3). As a result, virtually all significant delaminations or other anomalies in any component are detected and accurately located during inspection. For most inspections, trays 11 pass through inspection station only one time and proceed along inspection path 21 to another station 40 beyond tank 16. At station 40 the inspected trays are stacked, ready for removal.

FIG. 4 is a sectional elevation view of scanning station 30 taken approximately as indicated by line 4—4 in FIG. 1; however, the second receiver 28 shown in FIGS. 1–3 has been omitted in FIG. 4. Thus, FIG. 4 shows the tank 16 for coupling liquid 17. A liquid pump 52 having an inlet 54 is shown positioned within the liquid coupling medium 17 in tank 16. The outlet of the liquid pump 52 is connected by flexible conduit 23 to a housing 55 around the beam emission orifice 19 of transducer 18. Thus, as transducer 18 scans back and forth along the scanning path 37, all of the electronic components 14 on tray 11 are scanned in a predetermined pattern. It must be remembered that tray 11 is moving along the inspection path 21 (FIGS. 1 and 2), which path is perpendicular to the plane of FIG. 4. If the movement of tray 14 is continuous the scanning pattern is angled slightly, in the same manner as a television raster. See the scanning pattern 58, FIG. 4A. If the movement of the tray is intermittent, with a pause each time transducer 18 moves along its scanning path 37 between the extreme ends of that path (see phantom outlines 18A, 19A and 18B, 19B in FIG. 4) the scanning pattern is normalized, as shown by scanning pattern 59 in FIG. 4B. Either scanning pattern can be used; the normalized pattern 59 (FIG. 4B) produced by intermittent tray movement is preferred.

The flow of coupling liquid 17 downward from housing 55 onto the top of tray 11 serves a dual purpose. The coupling liquid, as previously noted, serves to couple the ultrasonic beam to the electronic components 14 under inspection. In addition, the flow of coupling liquid down onto the upper surfaces of the electronic components 14 urges those components downwardly, maintaining them in their desired positions in the receptacles 12 of tray 11.

FIG. 5 is a view similar to FIG. 4 but on a somewhat larger scale; FIG. 5 also shows a portion of the mechanism used to move tray 11 through system 20 (FIGS. 1 and 2) from the first station 20 through scanning station 30 and on to the second station 40. In the construction shown in FIG. 5, the lateral edges of tray 11 are supported on the upper runs of two continuous conveyor belts 62 and 63 located adjacent opposite sides of the elongated ultrasonic receiver 28. Belts 62 and 63 are driven simultaneously and at the same speed so that tray 11 and its cargo of electronic components 14 remains accurately aligned between two side rails 64 and 65. The speed for belts 62 and 63 should be adjustable to accommodate specific inspection needs. Rails 64 and 65 are mounted on two parallel frame members 66 and 67, respectively; frame members 66 and 67 are affixed to opposite ends of receiver 28 to maintain the receiver in fixed position at station 30, immersed in the coupling liquid 17 in tank 16. The liquid inlet 68 for receiver 28 also appears in FIG. 5. As previously noted, coupling fluid 17 is pumped into receiver 28 and flows upwardly out of the receiver against the bottom surfaces of the electronic components 14 on tray 11, thus coupling receiver 28 to the electronic components under inspection.

As is apparent from FIG. 5, belts 62 and 63 are subject to contact with coupling fluid 17, which may be water or at least an aqueous solution. The coupling fluid does not aid the conveyor belts in assuring consistent movement of tray 11 along its inspection path through station 30 (FIGS. 1 and 2). Rather, the liquid may make the belts slippery enough to interfere with consistent tray movement. This is minimized in part by the drying air from manifold 32, FIGS. 1 and 2, which blows the liquid from the belts. In some instances, particularly when each component 14 is to be scanned more than once, a second air drying manifold, located ahead of scanning station 30, may be desirable. It will be recognized that two or even more air dryers may be positioned on one or both sides of scanning station 30.

As shown in FIG. 5, each inspected component 14 has an internal level or plane 71; this is the plane to be inspected for circuit delaminations and other anomalies. When a focussed ultrasonic beam is employed, the beam from emission lens 19 is focussed approximately in this plane; the elevation of the unit comprising transducer 18 and lens 19 is adjustable upwardly and downwardly as indicated by arrows C to accommodate different levels of interest in components 14. Ordinarily, the transmission/reception unit 18,19 can be maintained at one elevation for all components 14, but a different electronic component may require vertical adjustment of the ultrasonic transmitter.

In some instances the force of the liquid cascading down from the transmitter/receiver 18,19 is not consistently adequate to keep the inspected components in a fixed pattern on tray 11, as is necessary for consistent inspection results. In such circumstances, an open mesh may be disposed over the tray to hold the electronic components in the desired pattern.

The operating frequency for the beam generated in the transmitter of unit 18 may vary substantially. Typically, a range of five to two hundred MHz may be employed. The trays 11 are usually of rather substantial size; a length of about five to thirteen inches (127–325 mm), a width of four to nine inches (101–228 mm) and a thickness of about 0.5 inch (25 mm), is typical. The number, shape, and size of receptacles 12 in a tray is determined by the size and shape of the components 14 being inspected. Of course, it is possible to utilize other means for advancing a tray 11 along its inspection path instead of belts 62 and 63; for example, a lead screw carriage mechanism or a linear motor with a carriage may be employed. A belt conveyor, as shown in the drawings, is usually preferable.

We claim:

1. A method of non-destructive ultrasonic inspection of a plurality of electronic components arranged in a predetermined pattern on a tray comprising the steps of:

A. advancing a tray bearing a plurality of electronic components in a predetermined pattern along a predetermined inspection path from a first station through a scanning station;

B. maintaining a flow of a coupling liquid medium from an ultrasonic transmitter toward the tray in the scanning station, along a beam path approximately normal to the inspection path;

C. energizing the ultrasonic transmitter to transmit an ultrasonic irradiation beam from the transmitter along the beam path to insonify electronic components on the tray in the scanning station;

D. moving the transmitter rapidly back and forth along a scanning path that is transverse to both the inspection path and the beam path;

E. collecting ultrasonic signals from the components on the tray at one end of the beam path;

F. processing the collected signals from step E to identify and locate delaminations in the electronic components; and G. blowing a drying gas onto the tray to remove the coupling fluid medium from the tray and from electronic the components on the tray.

2. A method of non-destructive ultrasonic inspection of a tray of electronic components according to claim 1 in which the ultrasonic signals collected in step E are reflected from the components on the tray.

3. A method of non-destructive ultrasonic inspection of a tray of electronic components according to claim 1 in which the ultrasonic signals collected in step E are transmitted through the components on the tray.

4. A method of non-destructive ultrasonic inspection of a tray of electronic components according to claim 1 in which the ultrasonic signals collected in step E include signals reflected from the components on the tray and signals transmitted through the components on the tray.

5. A method of non-destructive inspection of a tray of electronic components according to claim 1 in which the drying gas is air.

6. A method of non-destructive inspection of a tray of electronic components according to claim 1 in which:

the inspection is horizontal, the beam path is vertical, and the scanning path is horizontal.

7. An ultrasonic inspection apparatus for inspecting a plurality of electronic components positioned in a predetermined pattern upon a component-bearing tray, the inspection apparatus comprising:

tray advancing means for advancing a component-bearing tray, at a predetermined constant speed, along a horizontal inspection path from a first station through a scanning station, the tray advancing means comprising two conveyor belts located at opposite sides of the inspection path and equally spaced from the inspection path;

an ultrasonic transmitter, at the scanning station, having a beam emission orifice facing toward the inspection path but spaced therefrom;

energizing means for energizing the transmitter so that the transmitter transmits an ultrasonic irradiation beam along a vertical path from the transmitter toward the component-bearing tray to impinge upon and insonify each electronic component on the tray at the scanning station;

fluid flow means for maintaining a flow of an ultrasonic coupling fluid from the beam emission orifice of the ultrasonic transmitter onto one side of the tray in the scanning station;

means for moving the transmitter back and forth along a horizontal scanning path transverse to the inspection path; and an ultrasonic receiver located in the scanning station in position to intercept ultrasonic signals modified by the electronic components.

8. An ultrasonic inspection apparatus for inspecting electronic components, according to claim 7, in which the ultrasonic receiver is attached to and constitutes a part of the transmitter.

9. An ultrasonic inspection apparatus for inspecting electronic components, according to claim 7, in which the ultrasonic receiver is located on the opposite side of the inspection path from the transmitter.

10. An ultrasonic inspection apparatus for inspecting electronic components, according to claim 7, in which the tray advancing means moves the tray intermittently along the inspection path during intervals when the transmitter is at an end of the inspection path.

11. An ultrasonic inspection apparatus for inspecting electronic components, according to claim 7, and further comprising:

means to apply drying air to the tray at a location along the inspection path beyond the scanning station.

12. An ultrasonic inspection apparatus for inspecting electronic components, according to claim 7, and further comprising:

an open mesh, over the electronic components on the tray, for holding the components in a predetermined pattern.

13. An ultrasonic inspection apparatus for inspecting electronic components, according to claim 7, in which the receiver extends across the apparatus below the scanning path, and further comprising:

additional fluid flow means for maintaining a flow of an ultrasonic coupling liquid against the opposite side of a tray in the scanning station, above the receiver.

14. An ultrasonic inspection apparatus for inspecting electronic components, according to claim 13, in which the ultrasonic coupling liquid is continuously collected below the scanning station and recycled to the transmitter and to the receiver.

* * * * *